United States Patent [19]

Thekkadath

[11] Patent Number: 5,189,301
[45] Date of Patent: Feb. 23, 1993

[54] SIMPLE COMPACT ION MOBILITY SPECTROMETER HAVING A FOCUSING ELECTRODE WHICH DEFINES A NON-UNIFORM FIELD FOR THE DRIFT REGION

[75] Inventor: Govindanunny Thekkadath, Nepean, Canada

[73] Assignee: CPAD Holdings, Ltd., Canada

[21] Appl. No.: 747,857

[22] Filed: Aug. 20, 1991

[51] Int. Cl.$^5$ ............................................. H01J 49/40
[52] U.S. Cl. .................................... 250/287; 250/281; 250/286
[58] Field of Search ............... 250/287, 282, 288, 286, 250/281

[56] References Cited

U.S. PATENT DOCUMENTS

| | | | |
|---|---|---|---|
| 3,226,543 | 12/1965 | Melzner | 250/287 |
| 3,845,301 | 10/1974 | Wernlund et al. | 250/287 |
| 4,390,784 | 6/1983 | Browning et al. | 250/287 |
| 4,521,687 | 6/1985 | Naito | 250/296 |
| 4,551,624 | 11/1985 | Spangler et al. | 250/287 |
| 4,771,172 | 9/1988 | Weber-Grabau et al. | 250/282 |
| 4,777,363 | 10/1988 | Eiceman et al. | 250/286 |
| 4,855,595 | 8/1989 | Blanchard | 250/287 |
| 4,904,872 | 2/1990 | Grix et al. | 250/423 R |
| 4,950,893 | 8/1990 | Reategui et al. | 250/282 |

Primary Examiner—Jack I. Berman
Assistant Examiner—James Beyer
Attorney, Agent, or Firm—Scully, Scott, Murphy & Presser

[57] ABSTRACT

A compact ion mobility spectrometer (IMS) with increased sensitivity and resolution for detecting the composition of an unknown substance is disclosed. The IMS comprises a unitary cylindrical housing, inlet means for introducing sample gas, outlet means for withdrawing sample and drift gas, two high voltage electrodes, and a detector. The first electrode is pulsed to inject sample ions through an opening located in a second electrode which defines a drift region. The second electrode is cup-shaped having an open end and is electrically biased to create a non-uniform electric field gradient across said drift region. The electric field in said drift region is axial and radial resulting in an increase in ion drift velocity at the detector and a corresponding increase in detected peak signal amplitudes thereby increasing resolution. A shorter drift region and the absence of an aperture grid near the detector which cause ion collisional losses, helps to increase IMS sensitivity.

22 Claims, 5 Drawing Sheets

SIMPLE COMPACT ION MOBILITY SPECTROMETER HAVING A FOCUSING ELECTRODE WHICH DEFINES A NON-UNIFORM FIELD FOR THE DRIFT REGION

BACKGROUND OF THE INVENTION

1. Field of the Invention

This invention relates to ion mobility spectrometers and more particularly to an ion mobility spectrometer having an increased sensitivity that is compact and simple in design.

2. Description of the Prior Art

The ion mobility mass spectrometer (abbreviated as IMS) is an electrostatic analytical instrument which separates ions in terms of their mobility. A typical spectrometer, such as the prior art device illustrated in FIG. 1, has two contiguous cylindrical regions called the reaction and drift regions that are kept under a steady flow of usually atmospheric pressure nitrogen or air. Ions created in the reaction region of the spectrometer are pulsed into the drift region. Here they see a uniform axial electric field of about 300 volts/cm which causes them to travel with different speeds according to their mobility in the ambient gas, thus separating them according to their mobility. The drift velocity Vd of the ions can be expressed according to the relations shown in equations (1) and (2):

$$V_d = KE \qquad (1)$$

$$K = K_o (T/273)(760/P) \qquad (2)$$

where E is the electric field seen by the ions, T is the absolute temperature and P the pressure in torr of the drift gas. The constant of proportionality K is called the mobility of the ions. The reduced mobility $K_o$ takes into account variations in the mobility due to changes in temperature and pressure. The ions after reaching the end of the drift region impinge on a metal plate connected to a charge amplifier which gives a signal output proportional to the number of ions collected by the metal plate. The output from the amplifier consists of a series of voltage peaks separated in time, each peak corresponding to ions of a given mobility.

Figure 1:
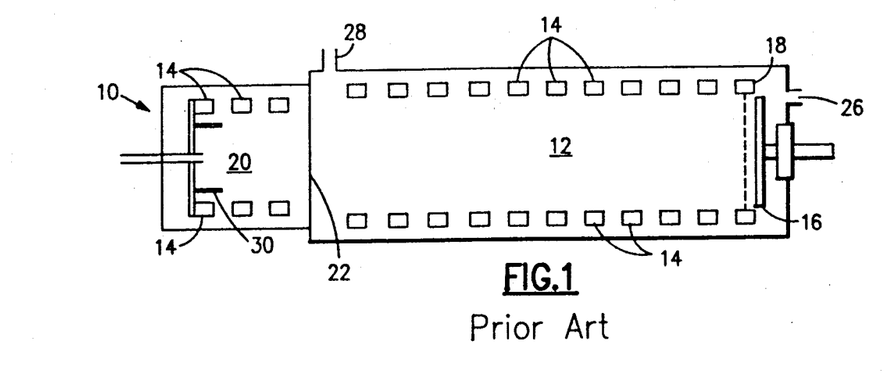
FIG. 1 is a design schematic of the ion mobility spectrometer of the prior art.

The reaction region has a weaker axial electric field, about 200 volts/cm. The reactant molecules are ionized in the reaction region using an electron source, usually a beta ray emitter like $^{63}Ni$. The product ions drift towards the end of the reaction region where an electrostatic shutter 22, called the Neilson-Bradbury shutter, is used to pulse the ions into the drift region. In its closed position the shutter is capable of producing an electric field transverse to the direction of motion of the ions. This deflects the ions away from the axis and neutralizes them thus preventing them from entering the drift region. The shutter is open when this transverse electric field is removed. This is usually achieved by electronically shorting the alternate wires in the shutter grid structure. By removing the transverse electric field, ions are allowed to enter the drift region. Typically the shutter is opened for a duration of 200 microseconds every 20 milliseconds.

DISCUSSION OF PRIOR ART

The prior art IMS 10, illustrated in FIG. 1, may vary in size from small (the size of a quarter) to the big (about 15 cm long and 3 cm in diameter) but all sizes have several common features. They all attempt to create a uniform electric field in the drift region 12. This is usually done by using a series of annular ring electrodes 14 with a constant potential difference between them. Some designs achieve the same result by using a resistive coating inside the drift tube with the voltage applied across the length of this coating. Another common design feature is the creation of a strong electric field near the detector plate 16 with the help of a grid 18 (called the aperture grid) placed very close to the detector plate. This improves the resolution of the instrument and thus its sensitivity by decreasing the effective input capacitance of the detector. The reaction region 20 also contains one or two annular electrodes 14 to create an axial electric field to transport the ions to the shutter region. The sample is usually injected into the reaction region at 24 with the drift gas entering the drift region 12 from the detector end 26 and exiting at the reaction end, as illustrated in FIG. 1. Another prior art IMS design mixes the sample with the drift gas and injects both from the detector end with the exit at the reaction end 28. All the designs use the same way of injecting the ions into the drift region using the Neilson-Bradbury shutter 22 as described above. Most of the designs use a Nickel source 30 for creating the electrons and ions in the reaction region. The electrons and ions can also be created by using thermal sources, uv sources, lasers, and corona ionization sources.

Although the IMS is simple in concept, the existing designs that have been patented or appear in the literature have not fully realized this simplicity in practice. As a result, high manufacturing costs prevent the IMS from becoming a mass produced device that could be used for a variety of monitoring needs.

Other disadvantages of the prior art IMS designs include the presence of the aperture grid near the detector which has been found to increase the noise due to microphonics caused by the capacitance of the aperture/detector plate combination. Signal loss is also inherent due to the collision of ions with the aperture grid. Also, because of the increased capacitance at the detector, the signal rise time is increased causing a decrease in the amplitude of received signals, and decreasing instrument resolution.

In view of the above-mentioned limitations of the conventional IMS design, an IMS having a more simplified design with increased sensitivity would be highly desirable. It is accordingly an object of the present invention to fulfill this need by providing an IMS that is more compact, easier to fabricate, has fewer components, and is cheaper to manufacture.

SUMMARY OF THE INVENTION

Figure 2:
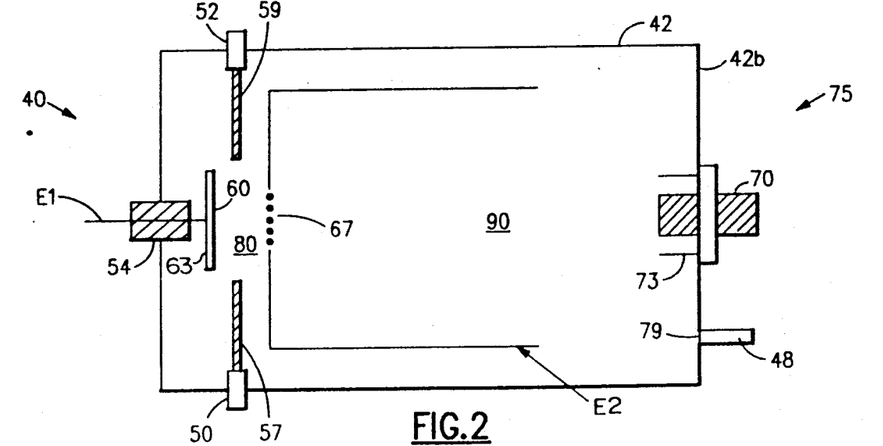
FIG. 2 is the design schematic of the ion mobility spectrometer of the present invention.

The IMS design of the present invention is shown in FIG. 2. There are three major changes in the design when compared to the conventional design. They are:

1. The absence of a multi-element electrode design to create the drift and reaction chambers, and especially, the absence of a uniform electric field in the drift region;

2. The absence of an aperture grid before the detector to increase the resolution and sensitivity; and 3. The absence of a reaction region as found in conventional IMS designs.

These simplifications do not decrease the resolution or the sensitivity of the instrument when compared to the earlier designs of the IMS. In the IMS design of the present invention, sensitivity is increased several fold due to the small sample volume and short transit times of the ions, and, the IMS resolution is improved.

The simplified IMS 40, as shown in FIG. 2, essentially consists of two high voltage electrodes E1 and E2 and a ground electrode which forms the gas container 42 and the detector holder. Electrode E1 is connected to a source of high voltage which can be pulsed.

Electrode E2 is kept at a constant high potential which is normally almost the same as electrode E1. It has dimensions which are calculated to yield a non-uniform electric field in the drift region which serves several purposes as will be explained hereinbelow.

DETAILED DESCRIPTION OF THE PREFERRED EMBODIMENTS

Figure 3:
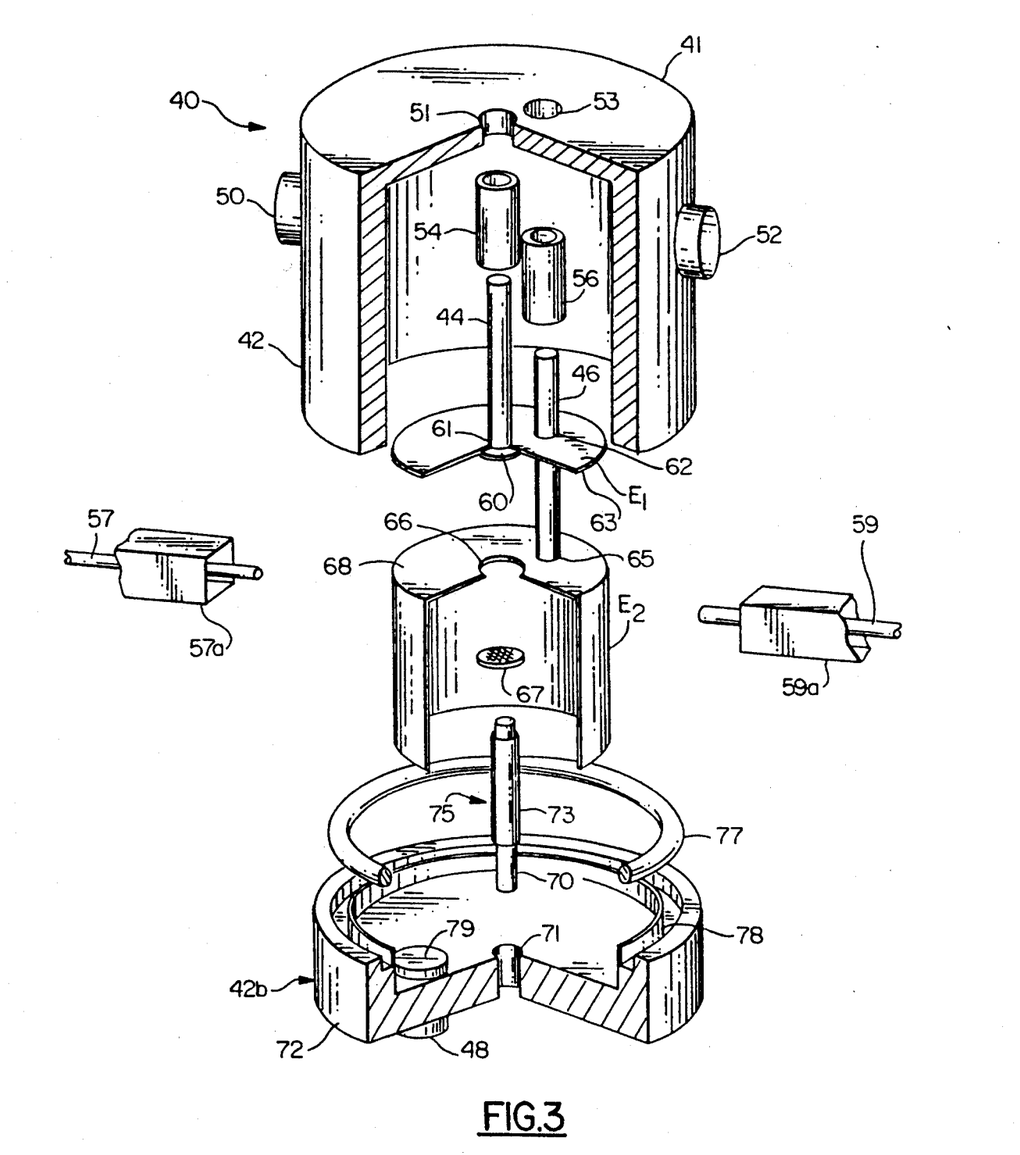
FIG. 3 is a three-dimensional exploded view of the ion mobility spectrometer of the present invention.

FIGS. 2 and 3 illustrate the preferred embodiment of the invention. FIG. 3 is an illustration of a three dimensional exploded view of the IMS 40 of the present invention. As illustrated in FIGS. 2 and 3, the IMS 40 consists of an external stainless steel container 42 at ground potential in which the electrodes and the detector are housed. The high voltage connections to electrodes E1 and E2 are the metal-ceramic feedthroughs 44, 54 and 46, 56 respectively. Feedthroughs 44 and 46 are extended to the outside of container 42 and are insulated therefrom. Container 42 has two holes 51 and 53 through end 41 to accommodate the feedthrough high voltage connections. Hole 51 accommodates feedthrough 44 which connects high voltage to electrode E1 and hole 53 accommodates feedthrough 46 which connects high voltage to electrode E2. Ceramic insulators 54 and 56 electrically isolate the high voltage feedthroughs 44 and 46 from container 42. Insulators 54 and 56 are cylindrical shaped and are at least as long as the container 42 is thick to ensure that the electrodes are not electrically shorted. Holes 51 and 53 in container 42 are just large enough to ensure a snug fit of the insulators 54 and 56 carrying feedthroughs 44 and 46. A metal ceramic seal is formed between the container 42 and the insulators 54 and 56. Though insulators 54 and 56 are ceramic in the preferred embodiment, other high voltage insulating material could be used.

Gas connections for inputting the sample packet and drift gas, and for outputting drift gas and non-pulsed sample ions are also provided at various locations on container 42. Gas connection 50 provides the support for sample inlet tube 57 to extend inside container 42. Sample inlet tube 57 functions to introduce the sample packet inside the IMS. Likewise, gas connection 52 provides support for outlet tube 59 which extends inside container 42 directly opposite that of inlet tube 57 as shown in FIG. 2. Outlet tube 59 provides the way for sample ions and drift gas to exit container 42 at connection 52. Gas connection 48 provides the means for drift gas to enter the IMS container 42 through inlet 79. It is shown in FIG. 3 adjacent to the outer edge of container end 72. Other locations for inputting drift gas into container 42 are equally suitable. Gas connections 48, 50 and 52 are all leak-tight and are preferably made of aluminum ferrules although similar compositions may be used. Sample inlet and outlet tubes 57, 59 are ceramic.

Electrode E1 is shown as a thin plate in FIG. 3. It is normally made of stainless steel although nickel or aluminum can also be used. In a preferred embodiment the diameter of electrode E1 is 40 mm. The metal ceramic high voltage feedthrough 44 is electrically connected to electrode E1 at 61 which is near the center of E1. Electrode E1 is physically supported by feedthrough 44. A hole 62 is located in electrode E1 for ceramic insulator 56 and high voltage feedthrough 46. As mentioned above, high voltage feedthrough 46 is connected to electrode E2, through ceramic insulator 56 and hole 62. Flush with the surface and at the center of electrode E1 is an ionizing source, which in the preferred embodiment is a $^{63}$Ni beta source 60.

Electrode E2, as shown in FIG. 3, is shaped like a cup. It is electrically connected to and physically supported by feedthrough 46 at 65. In the preferred embodiment, E2 surface 68 is located about 4 mm from E1. The length and diameter of E2 are substantially the same as the diameter of electrode E1, which is 36 mm in the preferred embodiment. A hole 66 is located substantially along the center axis of cylindrical electrode E2. The hole 66 is about 8 mm diameter and is the location where grid 67 is situated as shown in FIG. 2. The ions that are formed between E1 and E2 may easily pass through grid 67 when the voltages applied to E1 and E2 are conducive to pass through. The grid is preferably made of 200 mesh stainless steel and is about 8 mm in diameter.

Detector 75, as shown in FIGS. 2 and 3, is mounted along the axis of E1 and E2 at a distance of 30 mm from grid 67. It consists of a central electrode 70 made of stainless steel and is surrounded by a thin (0.3 mm thick) ground cylinder 73 of the same length. Central electrode 70 is preferably 1 mm in diameter while the ground cylinder 73 has an inner diameter of 2 mm. Separating central electrode 70 and ground cylinder 73 is an insulating metal ceramic seal (not shown). The whole detector assembly 75 is mounted through hole 71 formed in the end 72 of container base 42b. The detector ground cylinder 73 of detector 75 is fit into hole 71 and is electrically isolated from container base 42b by another metal ceramic seal (not shown). In the preferred embodiment, detector 75 is about 20 mm in length.

The IMS 40 can be heated by embedded cartridge heaters (not shown) in container 42. The two portions 42 and 42b are sealed together using a gold or aluminum seal 77 situated within grooved portion 78 of container 42. The IMS can also be heated by wrapping heaters around container 42. In both embodiments, the entire IMS is insulated using high efficiency high temperature insulation materials (not shown).

THEORY OF OPERATION

The sample to be tested is introduced into the IMS 40 through the sample inlet tube 57 as shown in FIG. 2.

The sample inlet tube 57 has a diameter of 0.5 mm in the preferred embodiment. A sample is introduced into the sample inlet tube 57 at a flow rate of a few cubic centimeters per minute. In the preferred embodiment, the desired flow rate is 10 cubic centimeters per minute. This flow is kept low to keep the sample volume in the ionizing region 80 to a minimum by reducing turbulence. This helps in producing a tight concentrated ion packet, which in turn improves the signal to noise ratio and therefore the sensitivity of the IMS 40. The outlet tube 59 for the drift and sample gases is a larger ceramic tube of 2.4 mm internal diameter and is located diametrically opposite inlet tube 57. That part of the sample which is not ionized therefore spends only the minimum possible time in the IMS 40, and if not ionized, is quickly exhausted through outlet tube 59, thereby reducing contamination of the inner walls of the IMS device. The drift gas, which is usually nitrogen, but which also can be air or any other inert gas of a high dielectric constant, is introduced through connector 48 near the detector 75 from the opposite side of tube 59 as shown in FIG. 3. Its flow rate is usually about three to five times that of the sample gas flow rate. The drift gas also helps to keep the inside of the IMS clean and provides a constant environment within the IMS.

There are essentially two regions in the IMS 40; the ionizing or reaction region 80 and the drift region 90. The ionizing region 80, best illustrated in FIG. 2, consists of the region bounded by the two electrodes E1 and E2 along their axis and is further limited by the size of the ionizing source 60 and the diameter of the sample stream emerging from inlet tube 57. In the preferred embodiment, a $^{63}$Ni beta source 60 is used as the ionizing source, although other means of ionization can also be used, for example, multiphoton or resonant laser ionization, field ionization, corona ionization, etc. Both positive and negative ions can be monitored depending on the sign of the potential applied to the IMS 40. The voltages on E1 and E2 are controlled using the pulsing circuit 43 which will b=hereinafter explained with respect to FIG. 4.

Figure 4:
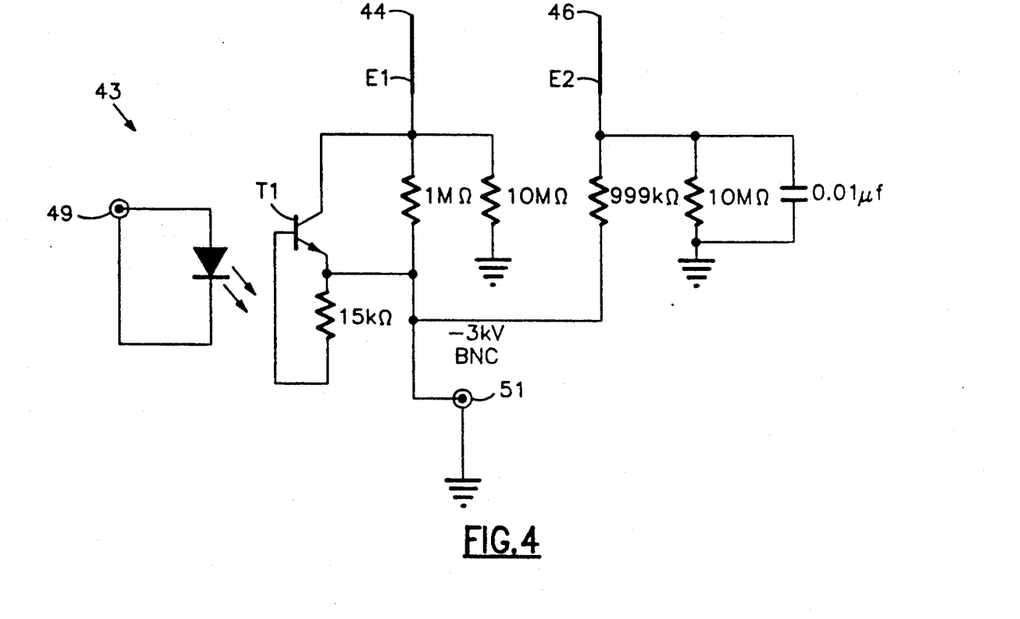
FIG. 4 is an electronic circuit diagram of the circuit used to pulse the voltages on each electrode.
Figure 5:
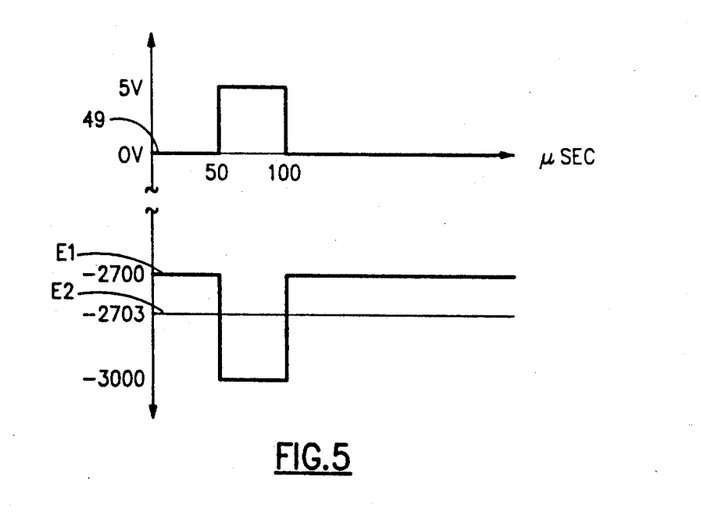
FIG. 5 is a graph of the voltages present at the trigger input and at each electrode in the circuit of FIG. 4.

As mentioned above, the high voltage connections are made at feedthroughs 44 and 46 as illustrated in FIG. 4. FIG. 5 is a plot of the voltages present at the electrodes and trigger input 49. When in the non-pulsed mode, the voltage at trigger input 49 remains at 0 volts. The voltage present at electrode E1 is normally at −2.7 kV and at electrode E2 is −2.703 kV when the IMS is non-pulsed. Normally, this results in a very weak electric field between E1 and E2 of about 10 to 20 v/cm, which is towards the plate of electrode E2, and which keeps the sample of negative ions from entering the drift region 90. This field is along the axis of the IMS 40. A −3.0 kV power supply source is shown at 51 in FIG. 4. Note that circuit 43 is illustrative of the pulsed high voltage circuit in the preferred embodiment, and that other circuit configurations can be used as well. In addition, both electrodes E1 and E2 can be biased to voltages within the range of −500 v to −6000 v but, in the preferred embodiment, −2.7 kV is the nominal value. The IMS 40 also can be used in the positive mode with all the voltage polarities reversed and reversing the connections to transistor T$_1$. The positive mode can be used for detecting the positive sample ions. When in the pulsed mode as shown in FIG. 5, the voltage at trigger input 49 rises to 5 V for a duration of nominally 50 μsec. Triggering could be activated by manual switch connected to a pulsed digital circuit (not shown).

While the trigger voltage at 49 is high, transistor T$_1$ is turned on so the voltage present at electrode E1 increases to −3 kV for a duration of 50 μsec. The voltage at electrode E2 remains constant. The jump in voltage at electrode E1 causes the electric field strength to reverse. The resulting field is about 3000 V/cm and is along the axis of the IMS but towards detector 75 so that the negative sample ions are pulsed into the drift region 90. The field is of such strength as to ensure that the sample ions are pulsed into the drift region 90 in a very short time compared to the drift time of the ions in the drift region. The pulsing circuit can be timed to generate a pulse at E1 of 50 μsec duration once every few milliseconds. Thus the electrodes E1 and E2 form a pulsed ion gun. The ions are pulsed from ionizing region 80 through grid 67 and drift towards the detector 75 in the non-uniform electric field created by the cup electrode E2 and the detector assembly 75. The electric field in the drift region 90 is determined by the dimensions of cup electrode E2 and detector 75.

Figure 7:
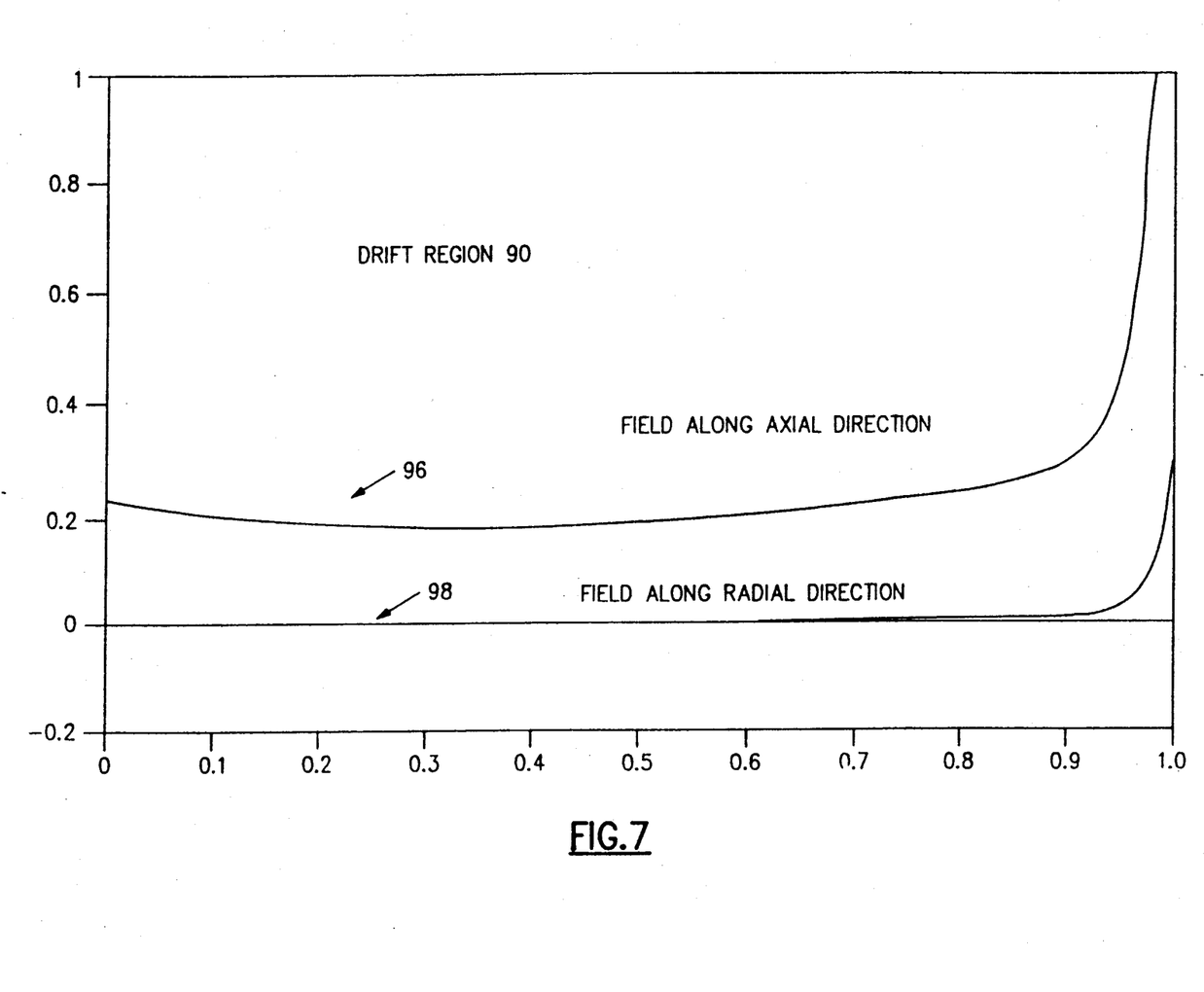
FIG. 7 is a graphic representation of the electric field strength in the axial and radial directions in the drift region of the present invention.

FIG. 7 illustrates the electric field strength 96 along the axial length of the drift region 90 of the present invention. As sample ions reach detector 75, the electric field 96 increases to about five times the value of the rest of the drift region 90. Thus, the drift velocity $V_d$ of the ions goes up substantially and the rate of change of induced current in the detector 75 also goes up in proportion.

Figure 6:
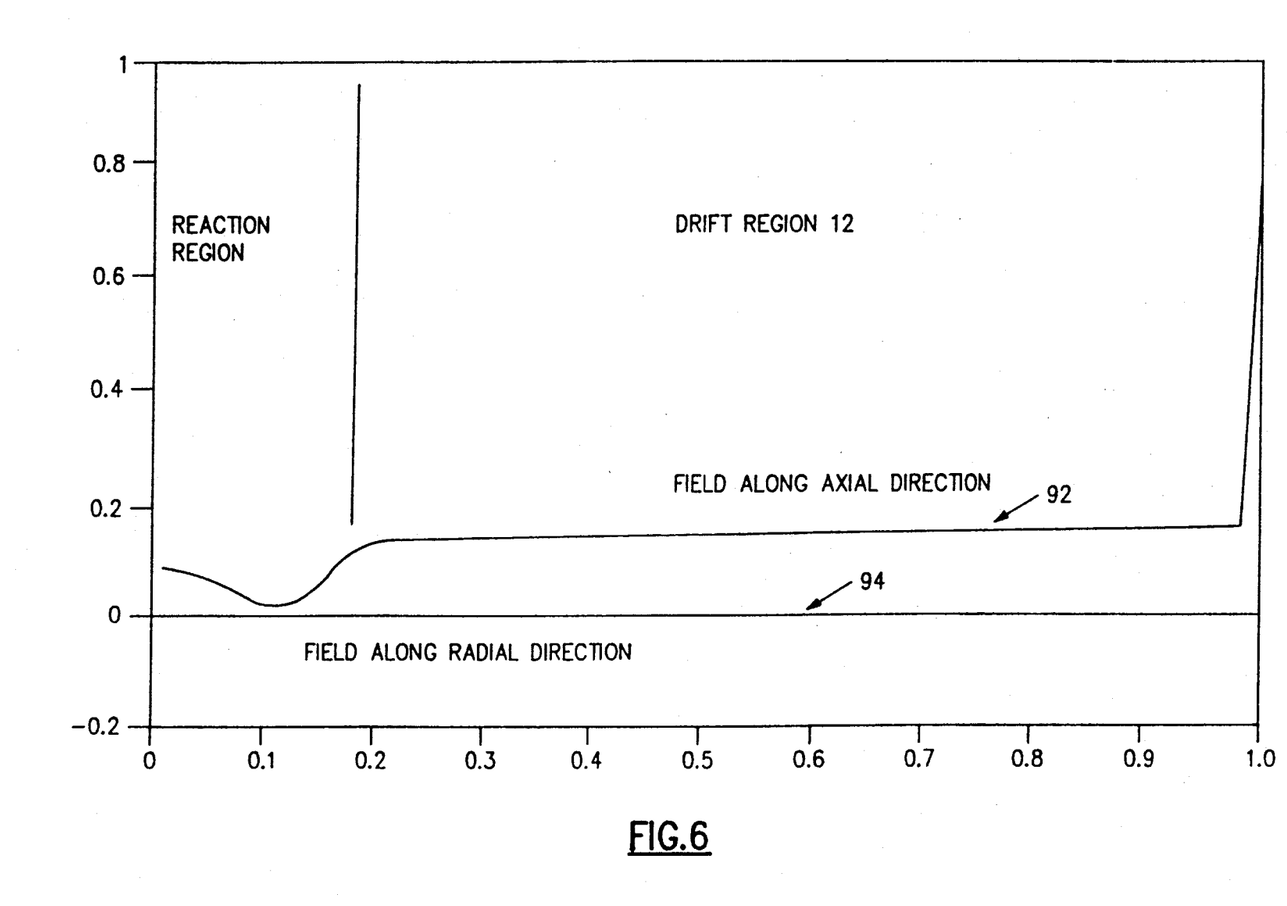
FIG. 6 is a graphic representation of the electric field strength in the axial and radial directions in the drift region of the prior art IMS.

As illustrated in FIG. 1, the prior art IMS utilized an extra electrode in the form of an aperture grid 18 in front of the detector 16. This design also caused an increase in the electric field near the detector 16. A plot of the electric field 92 along the axial length of the prior art IMS drift region 12 is shown in FIG. 6. The addition of aperture grid 18 in the prior art design also resulted in the loss of some signal at the detector 16 due to the collisional losses at the aperture grid. An increase in noise due to microphonics caused by the capacitance formed between the aperture grid 18 and the detector 16 also resulted. In addition, the increase in the capacitance at the detector 16 in the prior art IMS 10 resulted in an increase in the rise time of the signal. Since the total current induced in the detector by the ion cloud remains the same, increasing the rise time of the induced current in the prior art detector 16 decreases the peak height of the signal (since the area under the signal peak must remain the same).

In the IMS 40 of the present invention, much attention is paid to make the detector 75 physically very small and of a coaxial construction to reduce its capacitance. Because of the focusing field design of the drift region 90, the small size of the detector 75 does not result in any loss of ions reaching the detector. A comparison between the electric fields of the prior art design and the present invention, towards the axis in the radial direction, may be made by comparing the curve 98 in FIG. 7 (in the IMS of the present invention), with curve 94 in FIG. 6 (the prior art IMS). This comparison illustrates the focusing effect of the new configuration of cup electrode E2. Note that the electric field 98 increases along the radial axis of the IMS of the present invention, as ions drift towards the detector 75 end of drift region 90. This may be contrasted with the radial electric field 94 which is essentially non-existent in the prior art design. Thus the combination of the focusing effect and the much higher electric fields 96 and 98 near the detector 75 with a decrease in detector size results in a substantial increase in peak signal amplitudes with a corresponding decrease in their peak widths; This leads to an increase in instrument resolution. Since the background noise level is on the average a steady current, increases in the peak signal amplitude result in corresponding increases in the signal to noise ratio. A further increase in resolution is obtained by decreasing the fall time of the signal pulse. This is done by lowering the input resistance of the amplifier connected to detector 75 (not shown). Normally the amplifiers used with the IMS are of the electrometer type, that is, amplifiers having input resistances of the order of several tens of megohms. By using amplifiers of comparatively low input resistance, e.g., of the order of a few megohms, the RC time constant of the input is decreased. Consequently, the fall time of the signal is decreased by about ten times.

Resolution and Sensitivity

Resolution

The resolution R of the IMS 40 is defined as the ratio of the time t that the ion pulse takes to travel to the detector, to the temporal width W of the ion plane after traversing the distance L to the detector (Rokushika et al. 1985). This relation is shown in equation 3.

$$R = t/W \quad (3)$$

The width W of the ion plane is the geometric sum of its initial temporal width and the width due to diffusion broadening. Therefore, it is important to keep the initial width to a minimum to increase the resolution. When the initial width can be neglected with respect to the diffusion broadened width, the resolution can be expressed as shown in equation 4:

$$R = \{qEL/(44.2kT)\} \quad (4)$$

where q is the ionic charge, E the average electric field strength in the drift region, k the Boltzmann constant, and T the absolute temperature. Since EL is the total potential in the drift region, this equation tells us that the resolution is independent of the length of the IMS and increases in proportion to the voltage applied to the IMS. The cup IMS is designed to be used with voltages up to 6 kV or more, more than double that of the prior art devices. The size of the initial ion packet is kept small by using an axial field to eject the ions with the maximum velocity and by limiting the spatial spread of the sample with the help of a streamlined flow for the sample. Prior art devices used a passive technique to create the ion packet by switching off a transverse electric field, i.e, the Neilson-Bradbury shutter 22. The initial pulse width is assumed to be twice the gate width which, for a typical prior art IMS, is about 200 μSec. For an ion peak with a reduced mobility of 1.8 $cm^2V^{-1}s^{-1}$ and a drift length of 14 cm the diffusion contribution to the peak width is about 660 μsec. When the drift length is 5 cm, the diffusion width is only about 80 μsec. The initial time spread in the peak width should thus be kept well below 80 μsec to keep the IMS resolution to the maximum. Peak widths have been found at half maximum of 50 μsec for the chloride ion peak at 1.2 msec, which corresponds to a resolution of 24. Resolutions for prior art IMS are found to range from about 15 to 30. Further improvements in resolution are possible by reducing the contribution due to diffusion broadening and by reducing the initial pulse width. The resolution available now, coupled with the simplicity of construction of the cup electrode E2 in IMS 40, is adequate for most monitoring purposes including explosives detection.

Sensitivity

For a given mass of sample introduced into the IMS 40, the signal to noise ratio, and thus the minimum detectable levels and sensitivity of the IMS, will increase with the density of the ion packet produced in the IMS. Thus, an increase in sensitivity is inversely proportional to the volume of the sample. In the preferred embodiment of the IMS 40 this volume is kept to a minimum. The volume in which the ions originate is estimated to be about 30 μliters, which is about a thousand times smaller than the volume of the sample that could be introduced in the prior art IMS 10. Thus sensitivity is increased. The sample volume can be decreased even further by using a sample inlet and outlet tube 57a, 59a of rectangular cross section so that the sample flow is in the form of a thin sheet in a plane perpendicular to the axis of the IMS. Another factor in sensitivity stems from the losses suffered by the ion cloud when drifting towards the detector 75. Chemical reactions and collisional losses would be expected to go up with increasing drift time. These losses can be reduced by making the drift region 90 shorter and the cup electrode voltage at E2 higher. Since the drift time in IMS 40 is about ten times less than in the prior art IMS 10, the IMS 40 will have a correspondingly higher sensitivity. Preliminary measurements have shown that the signal strength due to the ion packet increases more than linearly with decreasing drift times.

Other embodiments can be made to improve the performance of the basic IMS 40 or to optimize it for use in special areas. For instance, scaling down the size of the IMS will increase its sensitivity. This is possible since the focusing effects are dependent only on the relative size of cup electrode E2 and detector assembly 75 dimensions.

Also, using higher voltages with drift gases of high dielectric breakdown strengths will increase the resolution and sensitivity.

What is claimed is:

1. A simplified ion mobility spectrometer having high sensitivity, said spectrometer comprising:
    (a) a cylindrical housing having an ionizing region at a first end thereof, a detection region at a second end thereof, and a drift region therebetween, said housing having means for introducing a drift gas at the second end thereof;
    (b) first means for introducing a sample gas, having molecules of interest therein, into the ionizing region at the first end of said housing, and second means for withdrawing sample gas and drift gas from said first end of said housing;
    (c) means for ionizing molecules of interest in said carrier gas within said ionizing region;
    (d) a first electrode means having an axial dimension for separating the ionizing region from the drift region, the configuration of which defines a non-uniform electric field gradient for said drift region, said field increasing in intensity along the axial dimension of the first electrode means towards the detection region, said first electrode means defining an aperture between said ionizing region and said drift region;

(e) means for detecting ionized molecules of interest mounted in said detection region adjacent said second end of said housing;

(f) means for intermittently pulsing ionized molecules in said ionizing region through said aperture into said drift region.

2. A simplified ion mobility spectrometer as claimed in claim 1, wherein said first electrode means is a cylindrical member having one end partially closed to separate said ionizing region from said drift region.

3. A simplified ion mobility spectrometer as claimed in claim 2, wherein said cylindrical member substantially encloses and defines said drift region.

4. A simplified ion mobility spectrometer as claimed in claim 1, wherein said means for intermittently pulsing said ionized molecules includes a pulsing electrode means between said housing and said first electrode.

5. A simplified ion mobility spectrometer as claimed in claim 4, wherein said pulsing electrode is planar and the electrode extends axially beyond the aperture defined in the first electrode.

6. A simplified ion mobility spectrometer as claimed in claim 3, wherein said means for detecting includes a circular and planar electrode coaxially aligned with said first electrode.

7. A simplified ion mobility spectrometer as claimed in claim 3, wherein said housing and said first electrode define an assembly having an inner drift region of 1 to 3 mm in diameter.

8. A simplified ion mobility spectrometer as claimed in claim 1, wherein said first means for introducing a sample gas is radially aligned with said cylindrical housing adjacent first end thereof.

9. A simplified ion mobility spectrometer as claimed in claim 8, wherein said second means is radially aligned with said cylindrical housing opposite said first means to facilitate removal of contaminants in said sample.

10. A low capacitance ion mobility spectrometer having a(simplified construction, said spectrometer comprising:

(a) a cylindrical housing member having first and second ends, said housing defining a sample inlet for sample gas at said first end and a drift gas inlet at said second end for drift gas;

(b) means for ionizing molecules of interest carried by said sample gas adjacent said inlet means;

(c) a cylindrical high potential electrode coaxially mounted within said cylindrical housing, said electrode defining a cylindrical axis with at least a portion of a drift region for ionized molecules of interest within said cylinder, the configuration of cylindrical electrode creating a non-uniform electric field gradient along said cylindrical axis in said drift region, said electrode defining an opening for said drift region adjacent the first end of said housing;

(d) a collector means mounted at said second end of said housing for receiving ionized molecules of interest from said drift region;

(e) means for pulsing ionized molecules of interest through said cylindrical electrode opening into said drift region.

11. A simplified ion mobility spectrometer as claimed in claim 10, wherein said cylindrical housing includes a unitary cylinder composed of stainless steel, closed at said first end.

12. A simplified ion mobility spectrometer as claimed in claim 10, wherein said means for pulsing ionized molecules is a first stainless steel electrode.

13. A simplified ion mobility spectrometer as claimed in claim 10, wherein said cylindrical electrode means is a unitary cylinder formed of stainless steel, and closed at said first end between said cylinder and said opening.

14. A simplified ion mobility spectrometer as claimed in claim 12, further comprising a first high voltage connector to said first stainless steel electrode and a second high voltage connector to said cylindrical electrode, wherein each of said first and second high voltage connectors extends respectively through a first and second ceramic feedthrough in said cylindrical housing.

15. A simplified ion mobility spectrometer as claimed in claim 14 wherein said cylindrical electrode is mounted on and supported by said second high voltage connector.

16. A simplified ion mobility spectrometer as claimed in claim 12, wherein said first and cylindrical electrodes are biased to a first and a second negative potential, and said first electrode is periodically pulsed to a negative potential below the potential on the cylindrical electrode.

17. A simplified ion mobility spectrometer as claimed in claim 15, wherein said housing is at ground and said first electrode is biased from 2700 volts to 3000 volts.

18. A simplified ion mobility spectrometer as claimed in claim 14, wherein said first and second feedthroughs are of a metal-ceramic construction.

19. A simplified ion mobility spectrometer as claimed in claim 10, wherein said sample inlet for introducing sample gas is mounted on the same axis as a sample outlet for withdrawing sample and drift gas.

20. A simplified ion mobility spectrometer as claimed in claim 19, wherein said sample inlet and said sample outlet are tubes having a rectangular cross section.

21. A simplified ion mobility spectrometer as claimed in claim 20, wherein said sample inlet and sample outlet are ceramic.

22. A simplified ion mobility spectrometer as claimed in claim 12, wherein said first and cylindrical electrodes are biased to a first and second positive potential and said first electrode is periodically pulsed to a positive potential above the potential on the cylindrical electrode.

* * * * *

UNITED STATES PATENT AND TRADEMARK OFFICE
CERTIFICATE OF CORRECTION

PATENT NO. : 5,189,301
DATED : February 23, 1993
INVENTOR(S) : Govindanunny Thekkadath It is certified that error appears in the above-identified patent and that said Letters Patent is hereby corrected as shown below:

Column 5, line 40: "b=" should read --be--
Column 9, line 35, Claim 9: after "means" insert --for withdrawing sample gas and drift gas--
Column 9, line 40, Claim 10: delete --(--

Signed and Sealed this

Twenty-third Day of November, 1993

Attest:

BRUCE LEHMAN

Attesting Officer       Commissioner of Patents and Trademarks